(12) United States Patent
Oishi et al.

(10) Patent No.: US 11,116,805 B2
(45) Date of Patent: Sep. 14, 2021

(54) PREVENTIVE AND THERAPEUTIC AGENT FOR CELIAC DISEASE

(71) Applicant: KABUSHIKI KAISHA YAKULT HONSHA, Minato-ku (JP)

(72) Inventors: Kenji Oishi, Minato-ku (JP); Hiroshi Makino, Minato-ku (JP); Akira Kushiro, Minato-ku (JP)

(73) Assignee: KABUSHIKI KAISHA YAKULT HONSHA, Minato-ku (JP)

( * ) Notice: Subject to any disclaimer, the term of this patent is extended or adjusted under 35 U.S.C. 154(b) by 81 days.

(21) Appl. No.: 15/527,616

(22) PCT Filed: Nov. 18, 2015

(86) PCT No.: PCT/JP2015/082423
§ 371 (c)(1),
(2) Date: May 17, 2017

(87) PCT Pub. No.: WO2016/080448
PCT Pub. Date: May 26, 2016

(65) Prior Publication Data
US 2017/0360852 A1 Dec. 21, 2017

(30) Foreign Application Priority Data
Nov. 19, 2014 (JP) .............................. JP2014-234387

(51) Int. Cl.
*A61K 35/745* (2015.01)
*A61K 39/05* (2006.01)
*A61K 35/00* (2006.01)
*C12N 1/20* (2006.01)

(52) U.S. Cl.
CPC ............ *A61K 35/745* (2013.01); *A61K 39/05* (2013.01); *C12N 1/20* (2013.01); *A61K 2035/115* (2013.01)

(58) Field of Classification Search
CPC .......... A01K 2267/01; A01K 2217/052; A01K 2227/30; C12N 15/8509; C12N 2800/90; C12N 2800/107; C12N 1/20; C12N 15/85; C12N 2830/15; C12N 2830/40; C12N 2830/46; C12N 2830/60; C12N 2830/90; C12N 2840/105; A61K 35/745; A61K 2300/00; A61K 35/744; A61K 35/747; A61K 35/741; A61K 35/74; A61K 31/201; A61K 36/06; A61K 41/004; A61K 45/06; A61K 9/48; C07K 14/61; C07K 16/00; C07K 16/3076; C07K 2317/21; C07K 2317/23; C07K 14/465; C07K 14/555; C07K 2319/43; C07K 2319/50; A23L 33/135; A23L 1/3014; A23L 33/10; A23L 33/21; A21D 8/045; A21D 13/04; A21D 13/066; A21D 8/042; A21D 10/00; A21D 10/025; A21D 13/047; A21D 13/40; A21D 2/36; C12P 39/00; C12P 7/6427; C12P 7/6472; A23Y 2220/03; A23Y 2220/15; A23Y 2220/17; A23Y 2220/29; A23Y 2220/67; A23Y 2240/75; A23Y 2300/29; A23Y 2300/45; A23Y 2300/55; A23Y 2280/00; A23V 2002/00; A23V 2200/3204; A23V 2200/324; C12R 1/01; C12R 1/225; C12R 1/23; C12R 1/245; C12R 1/25; C12R 1/44; C12R 1/46; A23P 10/30; Y02A 50/473
See application file for complete search history.

(56) References Cited

U.S. PATENT DOCUMENTS

| | | | |
|---|---|---|---|
| 2005/0031735 A1 | 2/2005 | Serata et al. | |
| 2007/0274955 A1 | 11/2007 | Gibson et al. | |
| 2008/0131556 A1 | 6/2008 | De Simone et al. | |
| 2008/0213320 A1* | 9/2008 | Eisenstein et al. | A61K 38/465 424/400 |
| 2008/0227165 A1* | 9/2008 | Mizusawa et al. | A23V 2002/00 435/134 |
| 2009/0087418 A1* | 4/2009 | Strozzi et al. | C12R 1/25 424/93.44 |
| 2010/0310520 A1 | 12/2010 | Sanz Herranz et al. | |
| 2012/0329059 A1 | 12/2012 | Sako et al. | |
| 2013/0004463 A1 | 1/2013 | Sugimoto et al. | |
| 2013/0209412 A1* | 8/2013 | Hoshi | A23C 9/1307 424/93.4 |
| 2015/0110771 A1* | 4/2015 | Garrido | A23L 33/195 424/94.61 |
| 2015/0351415 A1 | 12/2015 | De Simone et al. | |

FOREIGN PATENT DOCUMENTS

| | | | |
|---|---|---|---|
| EP | 1 443 105 A1 | 8/2004 | |
| EP | 1 930 407 A1 | 6/2008 | |
| JP | 3-49670 A | 3/1991 | |
| JP | 5-331036 A | 12/1993 | |
| JP | 2002-241292 A | 8/2002 | |
| JP | 2007-527199 A | 9/2007 | |
| JP | 2011-507540 A | 3/2011 | |
| JP | 2014-24776 A | 2/2014 | |
| WO | WO 03/040350 A1 | 5/2003 | |
| WO | WO 2006/097415 A1 | 9/2006 | |

(Continued)

OTHER PUBLICATIONS

International Search Report dated Feb. 23, 2016, in PCT/JP2015/082423 filed Nov. 18, 2015.

(Continued)

*Primary Examiner* — Sarvamangala Devi
(74) *Attorney, Agent, or Firm* — Oblon, McClelland, Maier & Neustadt, L.L.P.

(57) ABSTRACT

Provided is a novel preventive or therapeutic agent for celiac disease. A preventive or therapeutic agent for celiac disease, comprising at least one bacterium belonging to the genus *Bifidobacterium* selected from the group consisting of *Bifidobacterium breve* and *Bifidobacterium bifidum* and/or a processed bacterial cell thereof as an active ingredient.

8 Claims, 7 Drawing Sheets

(56) References Cited

FOREIGN PATENT DOCUMENTS

WO     WO 2011/039328 A1 *   4/2011
WO     WO 2011/083738 A1     7/2011

OTHER PUBLICATIONS

Medina et al., "Bifidobacterium strains suppress in vitro the pro-inflammatory milieu triggered by the large intestinal microbiota of coeliac patients", Journal of Inflammation, vol. 5, No. 19, (2008), 13 pages.
Cinova et al., "Role of Intestinal Bacteria in Gliadin-Induced Changes in Intestinal Mucosa: Study in Germ-Free Rats", PLoS ONE, vol. 6, Issue 1, e16169, (2011), pp. 1-10.
clinicaltrials.gov, "Probiotics for the Treatment of Irritable Bowel Syndrome in Celiac Patients (ProCel)", NCT01699191, (2012), 2 pages.
Partial Supplementary European Search Report dated Mar. 12, 2018 in European Patent application No. 15861084.0, 11 pages.
Extended European Search Report dated Jun. 19, 2018 in European Patent Application No. 15861084.0, 11 pages.

* cited by examiner

PREVENTIVE AND THERAPEUTIC AGENT FOR CELIAC DISEASE

TECHNICAL FIELD

The present invention relates to a preventive or therapeutic agent for celiac disease.

BACKGROUND ART

Celiac disease is a disease caused by an immune reaction to gluten, which is a group of proteins found in wheat and the like. Specifically, a part of gluten which cannot be degraded by human digestive enzymes is taken up in the form of undigested peptide chains by small intestinal epithelial tissues, resulting in an immune reaction, which triggers inflammation in small intestinal epithelial tissues. The symptoms of celiac disease manifest as a chronic bowel disease. The small intestinal epithelial tissues become inflamed, leading to malabsorption, chronic diarrhea, weight loss, abdominal distension, growth retardation, and the like.

Basically, the cure for celiac disease is eating gluten-free diet. However, since many foods contain gluten, a completely gluten-free dietary life is difficult. As a means for improving the symptoms of celiac disease, the use of certain bacteria belonging to the genus *Bifidobacterium* (*Bifidobacterium longum*) has been reported (Patent Literature 1). This is based on the finding that a specific bacterial strain of *Bifidobacterium longum* is capable of taking up and hydrolyzing gluten peptides, thereby reducing the toxicity of gluten peptides. Meanwhile, it has been reported that other bacteria belonging to the genus *Bifidobacterium* such as *Bifidobacterium bifidum* and *Bifidobacterium animalis* do not have such a toxicity-reducing effect (Patent Literature 1). Further, there is no report on the repairing action of bacteria belonging to the genus *Bifidobacterium* on small intestinal epithelial tissues having increased permeability due to gluten stimulation.

CITATION LIST

Patent Literature

Patent Literature 1: JP-A-2011-507540

SUMMARY OF THE INVENTION

Problems to be Solved by the Invention

An object of the present invention is to provide a novel preventive or therapeutic agent for celiac disease.

Means for Solving the Problems

In an attempt to achieve the aforementioned object, the present inventors studied the inhibitory action of various probiotics on the gluten stimulation-induced hyperpermeability of the small intestinal epithelial cell layer. As a result, they found that *Bifidobacterium breve* and *Bifidobacterium bifidum* had a potent inhibitory effect among other bacteria belonging to the genus *Bifidobacterium*. They further found that these bacteria also had a repairing action on the small intestinal epithelial cell layer having increased permeability due to gluten stimulation, thereby completing the present invention.

That is, the present invention provides the following [1] to [8].

[1] A preventive or therapeutic agent for celiac disease comprising at least one bacterium belonging to the genus *Bifidobacterium* selected from the group consisting of *Bifidobacterium breve* and *Bifidobacterium bifidum* and/or a processed bacterial cell thereof as an active ingredient.

[2] The preventive or therapeutic agent for celiac disease according to [1], wherein the bacterium belonging to the genus *Bifidobacterium* is at least one selected from the group consisting of *Bifidobacterium breve* YIT10001 (FERM BP-8205), *Bifidobacterium breve* YIT4065 (FERM BP-6223), *Bifidobacterium breve* YIT12272 (FERM BP-11320), *Bifidobacterium breve* DSM20213, *Bifidobacterium bifidum* YIT4007 (FERM BP-791), *Bifidobacterium bifidum* YIT10347 (FERN BP-10613), and *Bifidobacterium bifidum* DSM20456.

[3] Use of at least one bacterium belonging to the genus *Bifidobacterium* selected from the group consisting of *Bifidobacterium breve* and *Bifidobacterium bifidum* and/or a processed bacterial cell thereof for the production of a preventive or therapeutic agent for celiac disease.

[4] The use according to [3], wherein the bacterium belonging to the genus *Bifidobacterium* is at least one selected from the group consisting of *Bifidobacterium breve* YIT10001 (FERM BP-8205), *Bifidobacterium breve* YIT4065 (FERM BP-6223), *Bifidobacterium breve* YIT12272 (FERM BP-11320), *Bifidobacterium breve* DSM20213, *Bifidobacterium bifidum* YIT4007 (FERM BP-791), *Bifidobacterium bifidum* YIT10347 (FERN BP-10613), and *Bifidobacterium bifidum* DSM20456.

[5] At least one bacterium belonging to the genus *Bifidobacterium* selected from the group consisting of *Bifidobacterium breve* and *Bifidobacterium bifidum* and/or a processed bacterial cell thereof for use in preventing or treating celiac disease.

[6] The bacterium and/or a processed bacterial cell thereof according to [5], wherein the bacterium belonging to the genus *Bifidobacterium* is at least one selected from the group consisting of *Bifidobacterium breve* YIT10001 (FERN BP-8205), *Bifidobacterium breve* YIT4065 (FERM BP-6223), *Bifidobacterium breve* YIT12272 (FERM BP-11320), *Bifidobacterium breve* DSM20213, *Bifidobacterium bifidum* YIT4007 (FERM BP-791), *Bifidobacterium bifidum* YIT10347 (FERN BP-10613), and *Bifidobacterium bifidum* DSM20456.

[7] A method for preventing or treating celiac disease, comprising administering an effective amount of at least one bacterium belonging to the genus *Bifidobacterium* selected from the group consisting of *Bifidobacterium breve* and *Bifidobacterium bifidum* and/or a processed bacterial cell thereof.

[8] The method according to [7], wherein the bacterium belonging to the genus *Bifidobacterium* is at least one selected from the group consisting of *Bifidobacterium breve* YIT10001 (FERN BP-8205), *Bifidobacterium breve* YIT4065 (FERN BP-6223), *Bifidobacterium breve* YIT12272 (FERN BP-11320), *Bifidobacterium breve* DSM20213, *Bifidobacterium bifidum* YIT4007 (FERN BP-791), *Bifidobacterium bifidum* YIT10347 (FERN BP-10613), and *Bifidobacterium bifidum* DSM20456.

Effects of the Invention

The gluten stimulation-induced increase in the permeability of the small intestinal epithelial cell layer can be inhibited and the small intestinal epithelial cell layer having increased permeability can be repaired by ingesting the *Bifidobacte-*

*rium breve* or *Bifidobacterium bifidum* of the present invention, whereby celiac disease can be prevented or treated safely.

MODES FOR CARRYING OUT THE INVENTION

Figure 1:
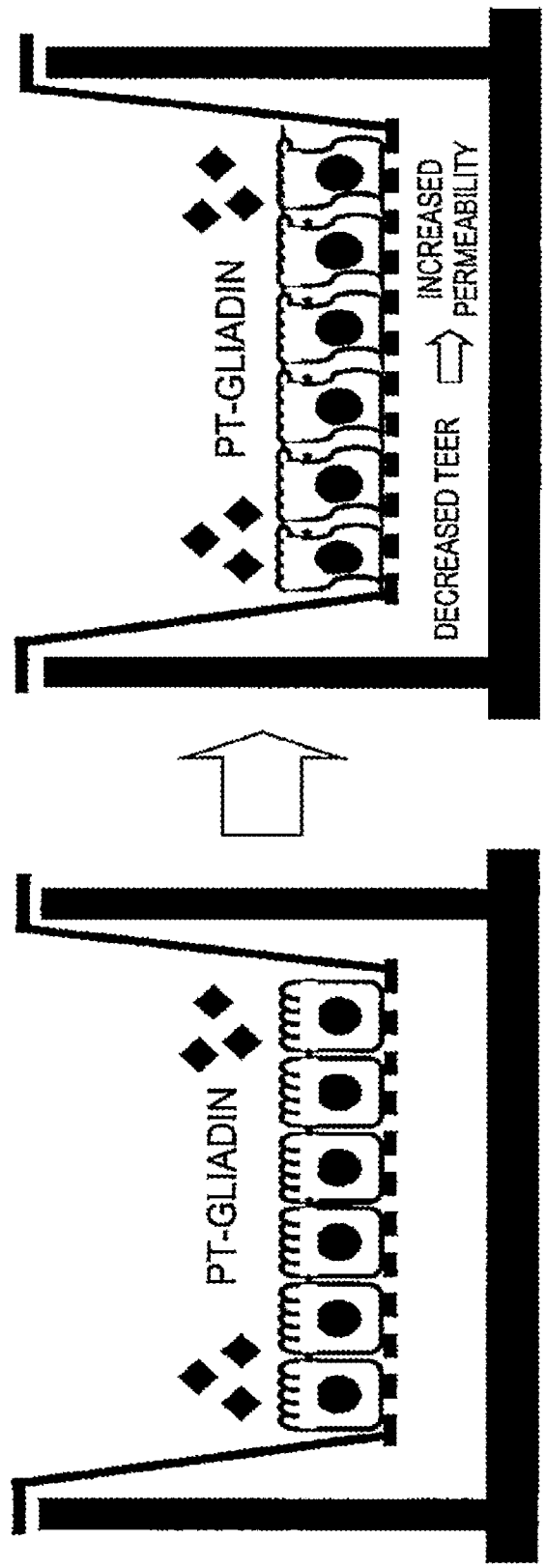
FIG. 1 illustrates the effect of pepsin-trypsin-digested gliadin (PT-gliadin) on the permeability of a Caco-2 monolayer (a schematic diagram of an experiment).

The active ingredient of the preventive or therapeutic agent for celiac disease of the present invention is at least one bacterium belonging to the genus *Bifidobacterium* selected from the group consisting of *Bifidobacterium breve* and *Bifidobacterium bifidum* and/or a processed bacterial cell thereof. Among these bacteria belonging to the genus *Bifidobacterium*, at least one selected from the group consisting of *Bifidobacterium breve* YIT10001 (FERM BP-8205), *Bifidobacterium breve* YIT4065 (FERM BP-6223), *Bifidobacterium breve* YIT12272 (FERM BP-11320), *Bifidobacterium breve* DSM20213, *Bifidobacterium bifidum* YIT4007 (FERM BP-791), *Bifidobacterium bifidum* YIT10347 (FERM BP-10613), and *Bifidobacterium bifidum* DSM20456 is preferable.

Also, since these bacteria or processed bacterial cells thereof act to suppress an inflammatory reaction in the lamina propria by inhibiting the enhanced production of TNF-α, which is an inflammatory cytokine, they can be utilized more safely for the prevention or treatment of celiac disease, which is an inflammatory disease.

Moreover, since these bacteria or processed bacterial cells thereof increase the production amount of IL-10 (anti-inflammatory cytokine), they can be utilized more safely and effectively for the prevention or treatment of celiac disease, which is an inflammatory disease.

Further, the bacteria belonging to the genus *Bifidobacterium* used as the active ingredient of the preventive or therapeutic agent for celiac disease of the present invention can also be utilized as an inhibitor of the increase in the permeability of the small intestinal epithelial cell layer caused by gluten stimulation and a permeability repairing agent for the small intestinal epithelial tissues having increased permeability for gluten.

A preparation method of the bacteria belonging to the genus *Bifidobacterium* used in the present invention is not particularly limited, and the bacteria can be prepared in accordance with a routine method.

For example, the bacteria belonging to the genus *Bifidobacterium* used in the present invention can be prepared by seeding and culturing the starter inoculum of the above bacteria in a medium allowing the growth of the bacteria, and then applying a means for isolating and purifying bacterial cells, such as centrifugation and filtration, upon completion of culture. Also, besides directly using the live bacterial cells thus obtained, the above bacteria can be prepared as freeze-dried bacterial cells, dead bacterial cells by subjecting the live bacteria to a treatment such as heat treatment or alcohol treatment, a culture containing the bacterial cells, an extract of the bacterial cells, a fraction of the extract, or, further, a processed product of the extract or fraction through processing such as pulverization, a mixture of these products, etc. for use.

Also, when an orally ingestible medium is used as the medium allowing the growth of the bacteria belonging to the genus *Bifidobacterium* during the preparation of the bacteria, a culture containing the bacteria can be used as the active ingredient of the preventive or therapeutic agent for celiac disease of the present invention directly or after a processing treatment such as heat treatment.

In this context, the medium allowing the growth of the bacteria belonging to the genus *Bifidobacterium* is not particularly limited, and examples thereof include a nutrient medium composed of various organic and inorganic sources of nutrient, such as a GAM medium, a MRS medium, and a BL medium. Further, besides these, animal milk such as cow milk and goat milk, a dairy product such as skimmed milk, powdered milk, dried skimmed milk, and fresh cream, and a soybean product such as soybean milk and soybean flour can also be used as a preferable medium. These media can be used directly or, for example, after diluting/concentrating to an appropriate concentration as needed. It is to be noted that the pH of the medium is not particularly limited.

In general, depending on the kind of medium, bacteria belonging to the genus *Bifidobacterium* do not always exhibit good proliferation performance. Therefore, it is preferable to add yeast extract, a soybean peptide, and further, a known growth promoter for bacteria belonging to the genus *Bifidobacterium* that can be a fermentation assisting agent, a reducing agent such as vitamin C, and the like to the above media, as needed.

Also, regular culture conditions can be applied to culture of bacteria belonging to the genus *Bifidobacterium* using the aforementioned media without any particular limitation.

That is, culture can be carried out by appropriately setting various conditions such as temperature, time, and incubation atmosphere to those that are suitable for bacteria belonging to the genus *Bifidobacterium* to be seeded in a medium. For example, incubation temperature may be 25 to 46° C., preferably 35 to 42° C., and incubation time may be 6 to 120 hours, preferably 24 to 72 hours. Also, as to the incubation atmosphere, culture is preferably carried out under anaerobic conditions, and for the culture method, any of, for example, static, stirring, and shaking cultures can be selected without particular limitation.

Also, the bacteria belonging to the genus *Bifidobacterium* used in the present invention can bring about the aforementioned desired effects through oral ingestion, regardless of whether they are alive and/or dead. Thus, not all of the bacteria belonging to the genus *Bifidobacterium* have to be alive when they are used in the present invention, and the aforementioned desired effects can still be obtained even when all or some of them are dead due to internal or external causes such as storage when they are used. Therefore, the bacteria belonging to the genus *Bifidobacterium* used in the present invention can be provided in the form suitable for pharmaceutical use after various processes (treatments).

The preventive or therapeutic agent for celiac disease of the present invention can be made into pharmaceutical compositions of various dosage forms with a pharmaceutically acceptable carrier in accordance with a routine method. Further, the aforementioned bacteria or a processed bacterial cell thereof can also be used as a food such as a functional food, health food, and food for specified health uses for the prevention or improvement of celiac disease.

For example, a granule, a tablet, and a capsule can be produced in accordance with a routine method by adding an excipient such as lactose, sucrose, sodium chloride, glucose, urea, starch, calcium carbonate, kaolin, crystalline cellulose, and silicic acid, a binder such as water, ethanol, propanol, a glucose solution, a starch solution, a gelatin solution, carboxymethylcellulose, methylcellulose, potassium phosphate, and polyvinylpyrrolidone, a disintegrant such as sodium alginate, catechin powder, sodium hydrogencarbonate, calcium carbonate, polyoxyethylene sorbitan fatty acid esters, and sodium lauryl sulfate, a humectant such as glycerin and starch, and a lubricant such as purified talc, a stearate, and polyethylene glycol to the aforementioned bacterial strains or products obtained from them (processed bacterial cells of these bacterial strains). Further, the tablet can be provided as a tablet that is coated with a common coating as needed such as a sugar-coated tablet, a gelatin-coated tablet, an enteric coated tablet, a film-coated tablet, or a double or multiple coated tablet. Further, examples of the form in which a food is provided include yogurt and a beverage.

Moreover, the preventive or therapeutic agent for celiac disease of the present invention may contain orally ingestible lactic acid bacteria which can impart beneficial functions to the living body.

The daily dosage of the aforementioned bacteria belonging to the genus *Bifidobacterium* in the preventive or therapeutic agent for celiac disease of the present invention cannot be determined in a definite way because the dosage varies according to the symptoms, age, body weight, and the like of an individual who ingests the agent. However, the daily dosage can be about $10^3$ to $10^{13}$ live and/or dead bacterial cells or such a number of processed bacterial cells that result from subjecting the above number of bacterial cells to processing.

EXAMPLES

Hereinbelow, the present invention will be described further in detail with reference to Examples; however, the present invention is not limited to these Examples in any way.

Example 1

A. Materials and Method
(1) Culture of Caco-2 and Production of a Monolayer

The human colon cancer-derived cell line, Caco-2, was purchased from DSMZ (Ref. No. ACC 169, Lot No. 10) and cultured in Dulbecco's Minimum Essential Medium (DMEM medium, the product of Sigma-Aldrich Corporation) containing 10% fetal calf serum (FCS, the product of Sigma-Aldrich Corporation). After 100% confluence was reached, the cells were further cultured overnight, and then collected by treatment with trypsin (a 0.25% Trypsin-EDTA solution, the product of Sigma-Aldrich Corporation). A $5.8 \times 10^5$ cells/mL cell suspension was prepared using a 10% FCS-added DMEM medium.

The Caco-2 monolayer was produced as follows using BD BioCoat™ HTS Caco-2 Assay System (the product of Becton, Dickinson and Company). Into each well in the upper layer of a 24-well BD BioCoat Fibrillar Collagen Cell Culture Insert plate, 0.34 mL of a $5.8 \times 10^5$ cells/mL cell suspension was added ($2.0 \times 10^5$ cells/well). In a tray in the lower layer, 30 mL of a 10% FCS-added DMEM medium was added, followed by incubation in a $CO_2$ incubator (5% $CO_2$, 95% Air, and 37° C.). After 48 hours, the media in the upper and lower layers were discarded by decantation, and 0.35 mL of Enterocyte Differentiation Medium containing MITO+ Serum Extender was added to each well in the upper layer. The same medium (30 mL) was also added to the tray in the lower layer, followed by incubation in a $CO_2$ incubator. After 24 hours, the media in the upper and lower layers were discarded by decantation, and Enterocyte Differentiation Medium containing MITO+ Serum Extender was added again in the same manner as the day before. After further incubation for 24 hours in a $CO_2$ incubator, the cells were used for permeability experiments.

(2) Preparation of Pepsin-Trypsin-Digested Proteins

Enzymatic digestion of wheat-derived gliadin (the product of Sigma-Aldrich Corporation) and bovine serum albumin (BSA, the product of Sigma-Aldrich Corporation) was carried out in accordance with the method of Lindfors, et al. [Clin. Exp. Immunol. 2008; 152: pp. 552 to 558]. Into 10 mL of 50 mM acetate buffer (pH 4.0), 60 mg of gliadin (or BSA) was suspended, and further, 3 mg of pepsin (the product of Sigma-Aldrich Corporation) was added, followed by incubation at 37° C. for two hours while shaking. To the resulting solution, 71 mg of $Na_2HPO_4$ was added, and the pH was adjusted to 7.0 with 2N NaOH. Subsequently, 3 mg of trypsin (the product of Sigma-Aldrich Corporation) was added, followed by incubation at 37° C. while shaking. After two hours, enzymes were inactivated by heating in a boiling water bath for 10 minutes. The resulting pepsin-trypsin-digested gliadin (PT-gliadin) and pepsin-trypsin-digested BSA (PT-BSA) were freeze-dried and then used in the experiments.

(3) Preparation of Heat-Killed Bacterial Cells

In the experiments, the heat-killed bacterial cells of *Bifidobacterium breve* YIT10001 (hereinbelow, BbY) were used. BbY was cultured at 37° C. for 18 hours in a 1% lactose-added modified GAM medium (the product of Nissui Pharmaceutical Co., Ltd) in an anaerobic glovebox.

Upon completion of culture, the bacterial cells were washed by centrifugation with sterile purified water. The washed bacterial cells were suspended in sterile purified water and heated at 100° C. for 30 minutes, and then freeze-dried.

(4) Measurement of the Permeability of the Caco-2 Monolayer (i) The Effect of Pepsin-Trypsin-Digested Proteins on the Permeability of the Monolayer After adding PT-gliadin or PT-BSA to the luminal side of the Caco-2 monolayer (upper layer), the changes in transepithelial electrical resistance (TEER) were measured over time. As shown in FIG. 1, TEER values decrease as the permeability of the monolayer increases due to incubation with PT-gliadin. Details of the experimental procedure will be described below.

The medium in the upper layer of the Caco-2 monolayer prepared in (1) above was discarded by decantation, and 0.35 mL of a DMEM medium containing the PT-gliadin or PT-BSA prepared in (2) above was added to each well. Into each well of the 24-well plate in the lower layer, 0.75 mL of a DMEM medium was added, and immediately after that, TEER was measured. Subsequently, culture was continued in a $CO_2$ incubator and TEER was measured over time. The amount of changes in TEER was expressed based upon TEER before initiation of incubation with PT-gliadin or PT-BSA taken as 100%. It is to be noted that cells to which a DMEM medium containing neither PT-gliadin nor PT-BSA was added were used as the negative control.

(ii) The Effect of BbY on the Gliadin Stimulation-Induced Hyperpermeability of the Monolayer After adding PT-gliadin and the heat-killed bacterial cells of BbY to the luminal side of the Caco-2 monolayer (upper layer), the changes in TEER were measured over time. It was presumed that if a decrease in TEER was inhibited in the presence of bacterial cells, the hyperpermeability of the monolayer was also inhibited. Details of the experimental procedure will be described below.

The medium in the upper layer of the Caco-2 monolayer prepared in (1) above was discarded by decantation, and 0.35 mL of a DMEM medium containing the PT-gliadin prepared in (2) above and the heat-killed bacterial cells prepared in (3) above was added to each well. Into each well of the 24-well plate in the lower layer, 0.75 mL of a DMEM medium was added, and immediately after that, TEER was measured. Subsequently, culture was continued in a $CO_2$ incubator and TEER was measured over time. The amount of changes in TEER was expressed based upon TEER before initiation of incubation with PT-gliadin and heat-killed bacterial cells taken as 100%. It is to be noted that cells to which only a DMEM medium was added were used as the negative control, and cells to which a medium containing only PT-gliadin was added were used as the positive control.

(iii) The Effect of BbY on the Monolayer Having Increased Permeability Due to Gliadin Stimulation The hyperpermeable state was created by adding PT-gliadin to the luminal side of the Caco-2 monolayer (upper layer), followed by incubation. Subsequently, gliadin in the upper layer was washed away and then the heat-killed bacterial cells of BbY were added, and the changes in TEER were examined over time. It was presumed that if TEER was increased due to incubation with the bacterial cells, the hyperpermeability of the monolayer was repaired. Details of the experimental procedure will be described below.

The media in the upper and lower layers of the Caco-2 monolayer prepared in (1) above were discarded by decantation, and 0.35 mL of a DMEM medium containing the PT-gliadin prepared in (2) above was added to each well in the upper layer. Subsequently, into each well of the 24-well plate in the lower layer, 0.75 mL of a DMEM medium was added, and the cells were cultured in a $CO_2$ incubator for three hours. Then, TEER was measured, and the media in the upper and lower layers were discarded by decantation. Subsequently, 0.5 mL of a fresh DMEM medium was added to the upper layer, and the medium was discarded again by decantation. This operation was repeated again to remove PT-gliadin in the upper layer, and then 0.35 mL of a medium containing the heat-killed bacterial cells of BbY prepared in (3) above was added to each well in the upper layer. Then, 0.75 mL of DMEM was added to each well in the lower layer, and immediately after that, TEER was measured. Subsequently, culture was continued in a $CO_2$ incubator and TEER was measured over time. It is to be noted that cells to which only a DMEM medium was added throughout the experiment were used as the negative control and cells to which a DMEM medium containing no heat-killed bacterial cells was added after incubation with PT-gliadin were used as the positive control.

B. Results (1) The Effect of PT-Gliadin and PT-BSA on the Permeability of the Caco-2 Monolayer After adding PT-gliadin or PT-BSA to the luminal side of the Caco-2 monolayer, the effect of these proteins on mucosal permeability was examined using the changes in TEER after the addition as an index.

Figure 2:
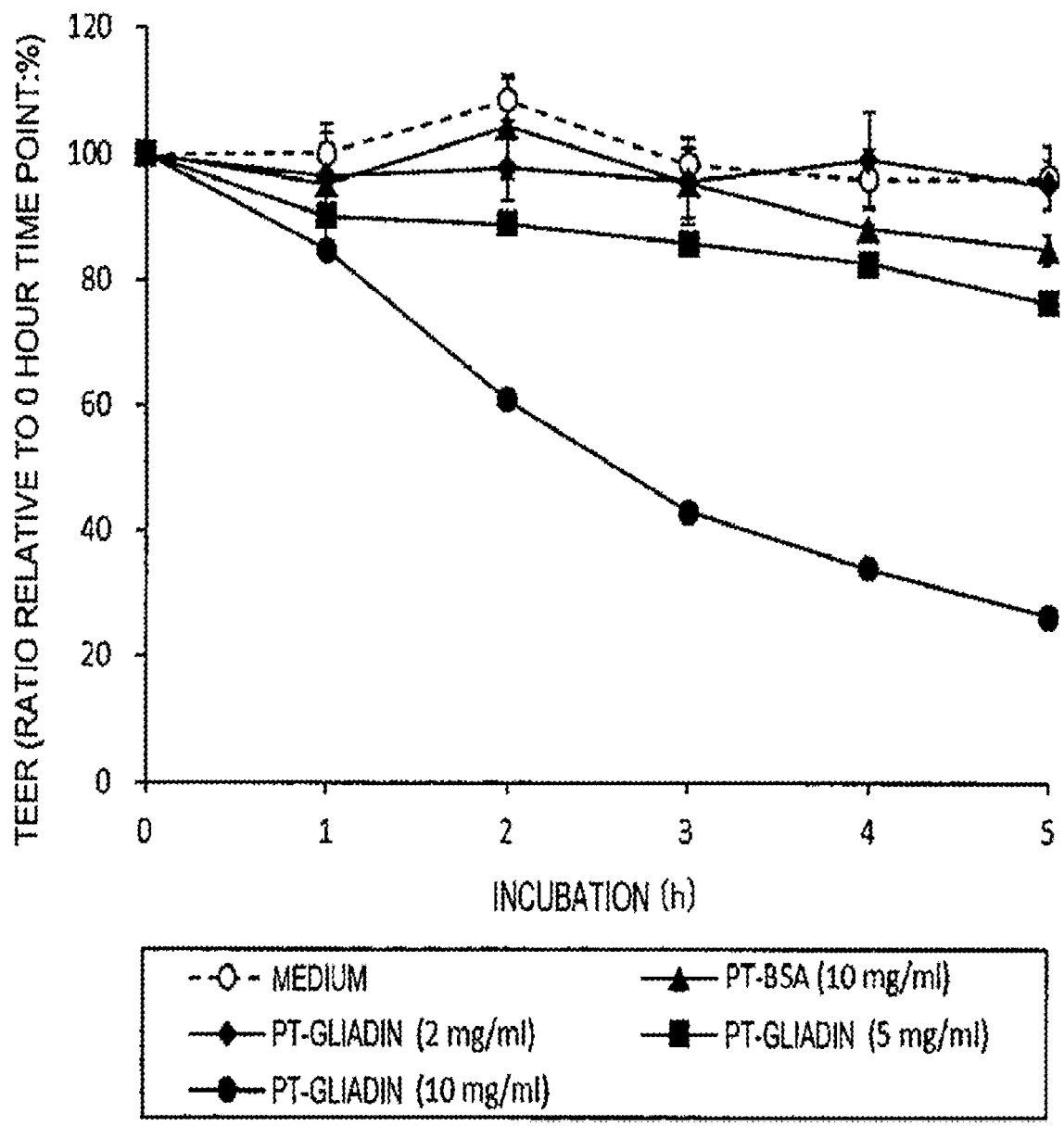
FIG. 2 illustrates the effect of PT-gliadin and pepsin-trypsin-digested BSA (PT-BSA) on the permeability of a Caco-2 monolayer. After adding PT-gliadin or PT-BSA to the luminal side of a Caco-2 monolayer, transepithelial electrical resistance (TEER) was measured over time.

As shown in FIG. 2, when the cells were incubated in a DMEM medium alone, there was very little change in TEER. When PT-gliadin was added at a concentration of 10 mg/mL, TEER was decreased with time, and after five hours, it was decreased to 26% of the initial value. Also, when PT-gliadin was added at concentrations of 2 mg/mL and 5 mg/mL, TEER was decreased to 96% and 77% of the initial value, respectively, after five hours, showing that the permeability-increasing action was dose-dependent. However, the changes observed at these concentrations were much smaller than those observed at a concentration of 10 mg/mL. Meanwhile, even when PT-BSA was added at a concentration of 10 mg/mL, there was very little change in permeability.

As shown above, the hyperpermeability of the Caco-2 monolayer was a phenomenon that was observed specifically when PT-gliadin was present in the luminal side. It was determined that PT-gliadin should be added to the luminal side at a concentration of 10 mg/mL for analyzing how various microorganisms affect gliadin stimulation-induced hyperpermeability.

Figure 3:
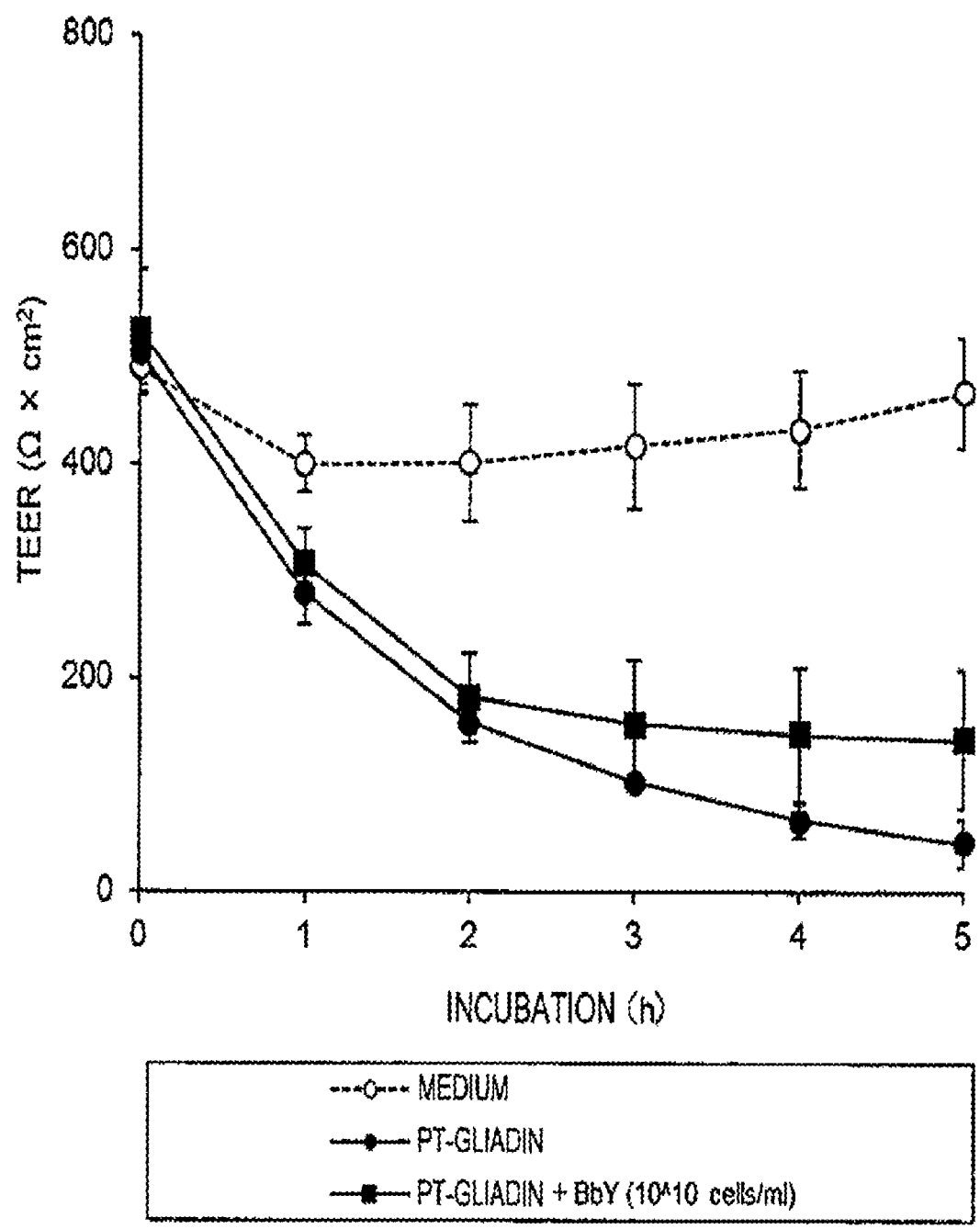
FIG. 3 illustrates the effect of heat-killed bacterial cells of *Bifidobacterium breve* YIT10001 (BbY) on the PT-gliadin stimulation-induced hyperpermeability of a Caco-2 monolayer. After adding PT-gliadin and heat-killed bacterial cells of BbY to the luminal side of a Caco-2 monolayer, TEER was measured over time. The figure shows the average TEER of three experiments and the standard deviation.

(2) The Effect of BbY on the Gliadin Stimulation-Induced Hyperpermeability of the Caco-2 Monolayer In the coexistence of the heat-killed bacterial cells of BbY and PT-gliadin, the decrease in TEER was inhibited at a concentration of $10^{10}$ cells/mL (FIG. 3). The percentage inhibition of decrease in TEER after five hours of incubation was 23%.

(3) The Effect of BbY on the Monolayer Having Increased Permeability Due to Gliadin Stimulation The hyperpermeable state was created by adding PT-gliadin to the luminal side of the Caco-2 monolayer, followed by incubation for three hours. Subsequently, PT-gliadin was washed away and the heat-killed bacterial cells of BbY were added, and the changes in TEER thereafter were measured over time.

Figure 4:
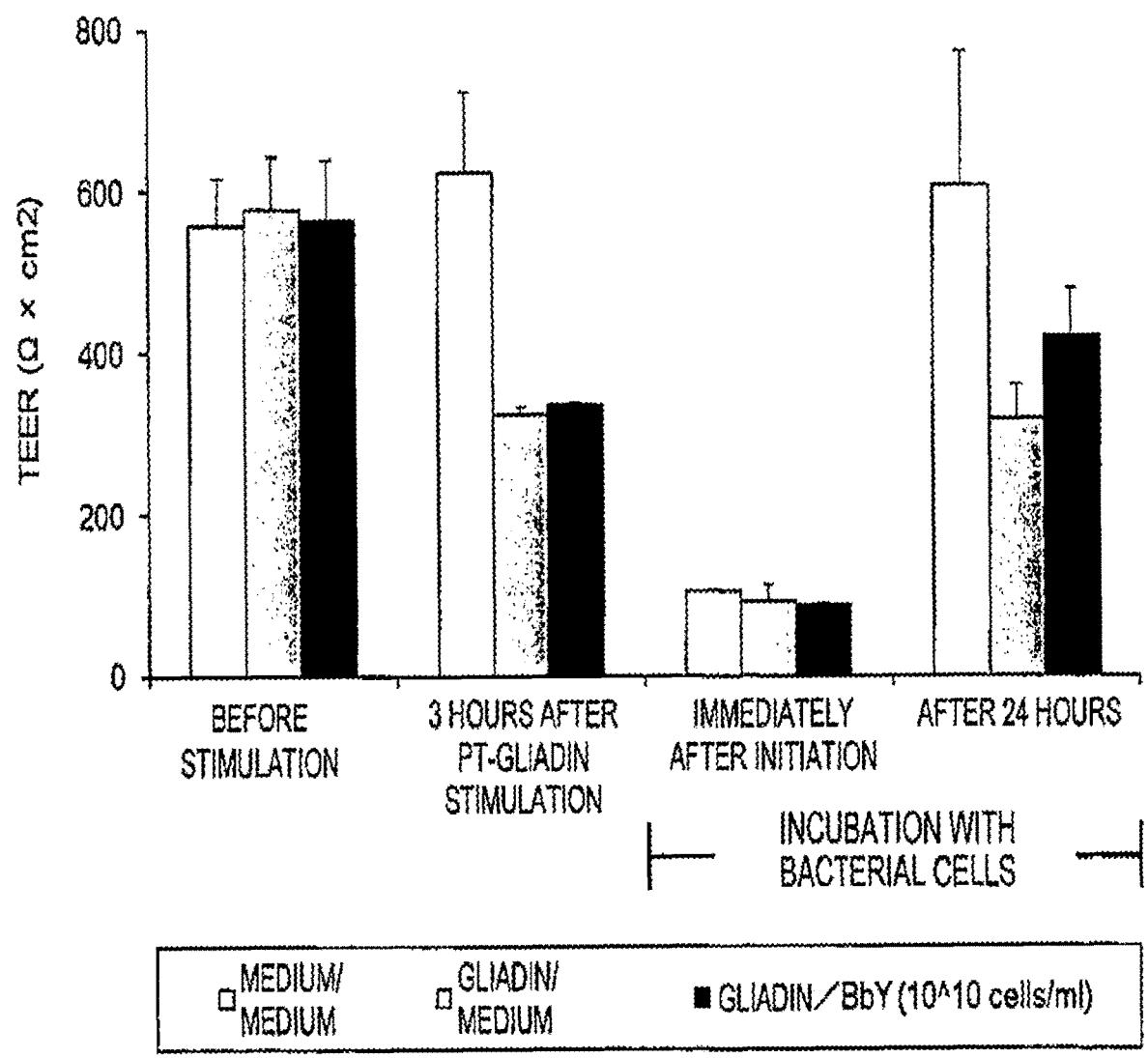
FIG. 4 illustrates the effect of heat-killed bacterial cells of BbY on the PT-gliadin stimulation-induced hyperpermeability of a Caco-2 monolayer. The hyperpermeable state was created by adding PT-gliadin to the luminal side of a Caco-2 monolayer, followed by incubation for three hours. Subsequently, PT-gliadin was washed away, and heat-killed bacterial cells of BbY were added to the luminal side of the monolayer, and TEER was measured over time. The figure shows the average TEER of three experiments and the standard deviation.

TEER of the Caco-2 monolayer before PT-gliadin stimulation was 570 $\Omega \times cm^2$ on average (FIG. 4, before stimulation), and after three hours of incubation, it was decreased to an average of 330 $\Omega \times cm^2$ (about 60%) (FIG. 4, 3 hours after PT-gliadin stimulation). Subsequently, the medium in the luminal side of the Caco-2 monolayer was discarded by decantation and replaced by a fresh DMEM medium. This operation was repeated to remove PT-gliadin, and then a medium containing the heat-killed bacterial cells of BbY was added, and immediately after that, TEER was measured. As a result, regardless of the presence or absence of the bacterial cells, TEER was drastically decreased in all the culture wells (FIG. 4, immediately after initiation of incubation with bacterial cells). The Caco-2 monolayer used in this experiment has such a property that its TEER greatly decreases upon contact with the air. Although the medium in the luminal side was exchanged once in the experiment (2) above, no decrease in TEER was observed. Meanwhile, in this experiment, washing with a DMEM medium was conducted twice to remove PT-gliadin, and the medium was exchanged three times in total. It was presumed that these operations increased the opportunity for the cells to be exposed to the air, leading to the marked decrease in TEER. The same experiment was repeated three times, and a marked decrease in TEER was similarly observed in all the experiments.

24 hours after the medium exchange, TEER of the Caco-2 monolayer that was not preincubated with PT-gliadin was recovered to the value three hours after PT-gliadin stimulation (FIG. 4, medium/medium). TEER of the Caco-2 monolayer to which a DMEM medium was added after preincubation with PT-gliadin was also increased over time (FIG. 4, gliadin/medium). However, the value after 24 hours was equal to the value three hours after PT-gliadin stimulation, and was not increased any further. From these results, it was considered that while a transient decrease in TEER due to medium exchange was recovered after 24 hours of incubation, PT-gliadin-induced injury remained without being repaired.

When the Caco-2 monolayer was incubated with BbY ($10^{10}$ cells/mL), the recovery of TEER was facilitated, reaching a value much higher than the value three hours after PT-gliadin stimulation (FIG. 4). This result suggests that the monolayer having increased permeability due to PT-gliadin stimulation was repaired by BbY.

As shown above, BbY not only inhibited the PT-gliadin stimulation-induced hyperpermeability of the small intestine mucous membrane, but also exhibited a repairing effect on the injured mucous membrane. Based on these findings, BbY is considered to serve as a probiotic effective for the prevention or treatment of celiac disease.

Example 2

In a similar manner to Example 1 (iii), the effect of various bacteria belonging to the genus *Bifidobacterium* on the monolayer having increased permeability due to gliadin stimulation was examined.

Figure 5:
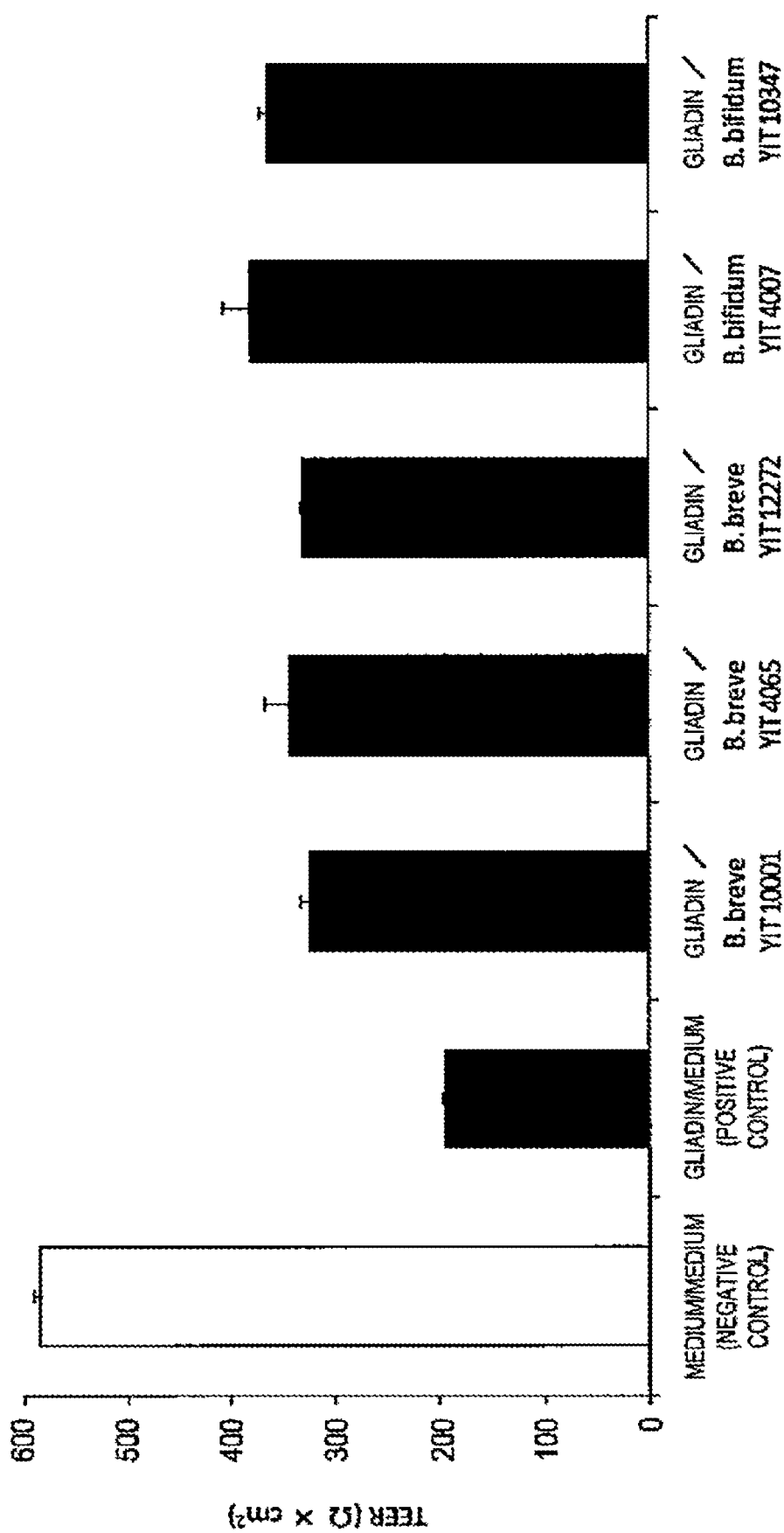
FIG. 5 illustrates the repairing effect of various *Bifidobacterium* bacterial strains on a Caco-2 monolayer having increased permeability due to gliadin stimulation. The bars show the average TEER of three experiments and the error bars show the standard deviation.

In the Caco-2 monolayer to which a DMEM medium containing the heat-killed bacterial cells of *Bifidobacterium breve* YIT10001 (*B. breve* YIT10001) was added, TEER was higher than that of the positive control (a DMEM medium was added alone after PT-gliadin stimulation) (FIG. 5, gliadin/*B. breve* YIT 10001). From this result, it was considered that the monolayer having increased permeability due to PT-gliadin stimulation was repaired by the addition of the above bacterial strain. Similar repairing effect was also observed in the Caco-2 monolayers incubated with bacterial strains other than *B. breve* YIT10001 (FIG. 5).

Figure 6:
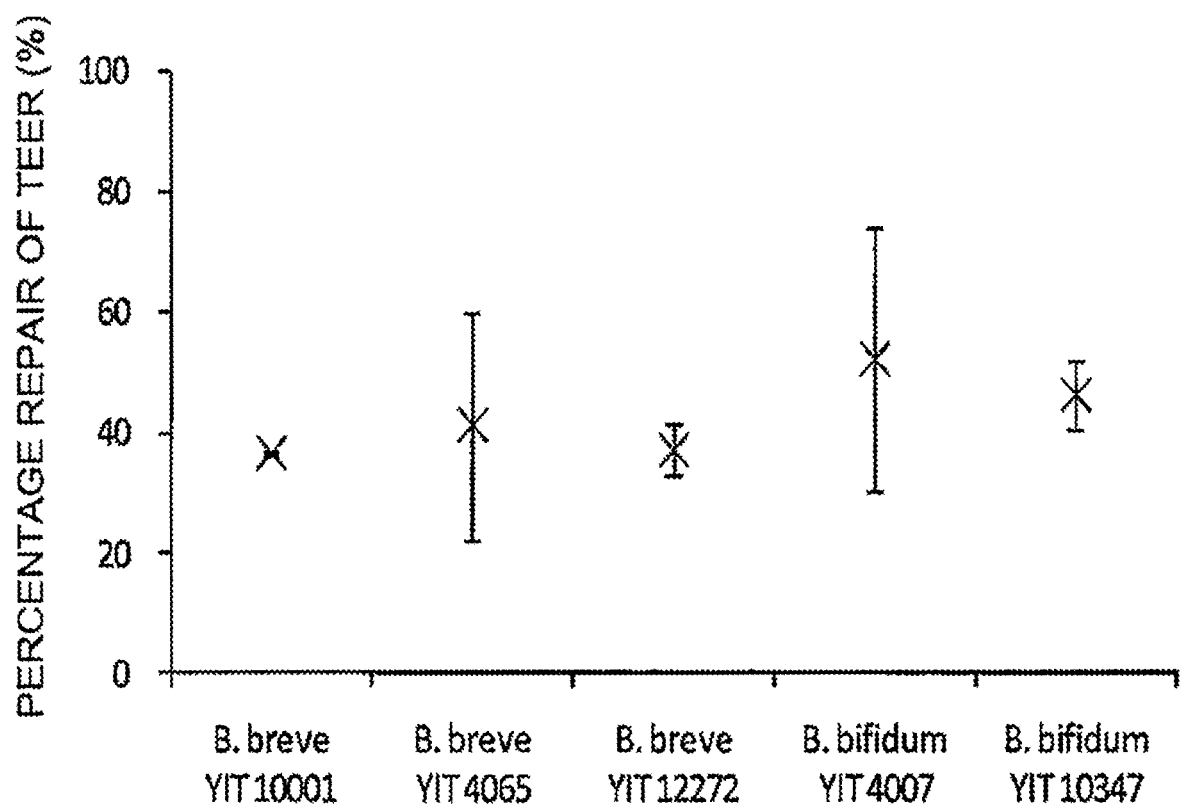
FIG. 6 illustrates the percentage repair of a Caco-2 monolayer by various *Bifidobacterium* bacterial strains. The symbol x indicates the average value of three experiments and the error bars show a 95% confidence interval for the average value. The t-test was used for statistical analysis.

The percentage repair of the monolayer by the addition of various strains of *Bifidobacterium* spp. was compared (FIG. 6). The average percentage repair by each of three bacterial strains of *B. breve* was about 40%. The average percentage repair by each of two bacterial strains of *B. bifidum* was about 50%, which was slightly higher than that by *B. breve*. Although *B. breve* YIT4065 and *B. bifidum* YIT4007 exhibited larger variations in percentage repair between experiments compared to the rest of the bacterial strains, the lower limit of the 95% confidence interval for the average value was above 0%. From this, it was confirmed that all of the bacterial strains significantly repaired the Caco-2 monolayers having increased permeability due to gliadin stimulation.

Figure 7:
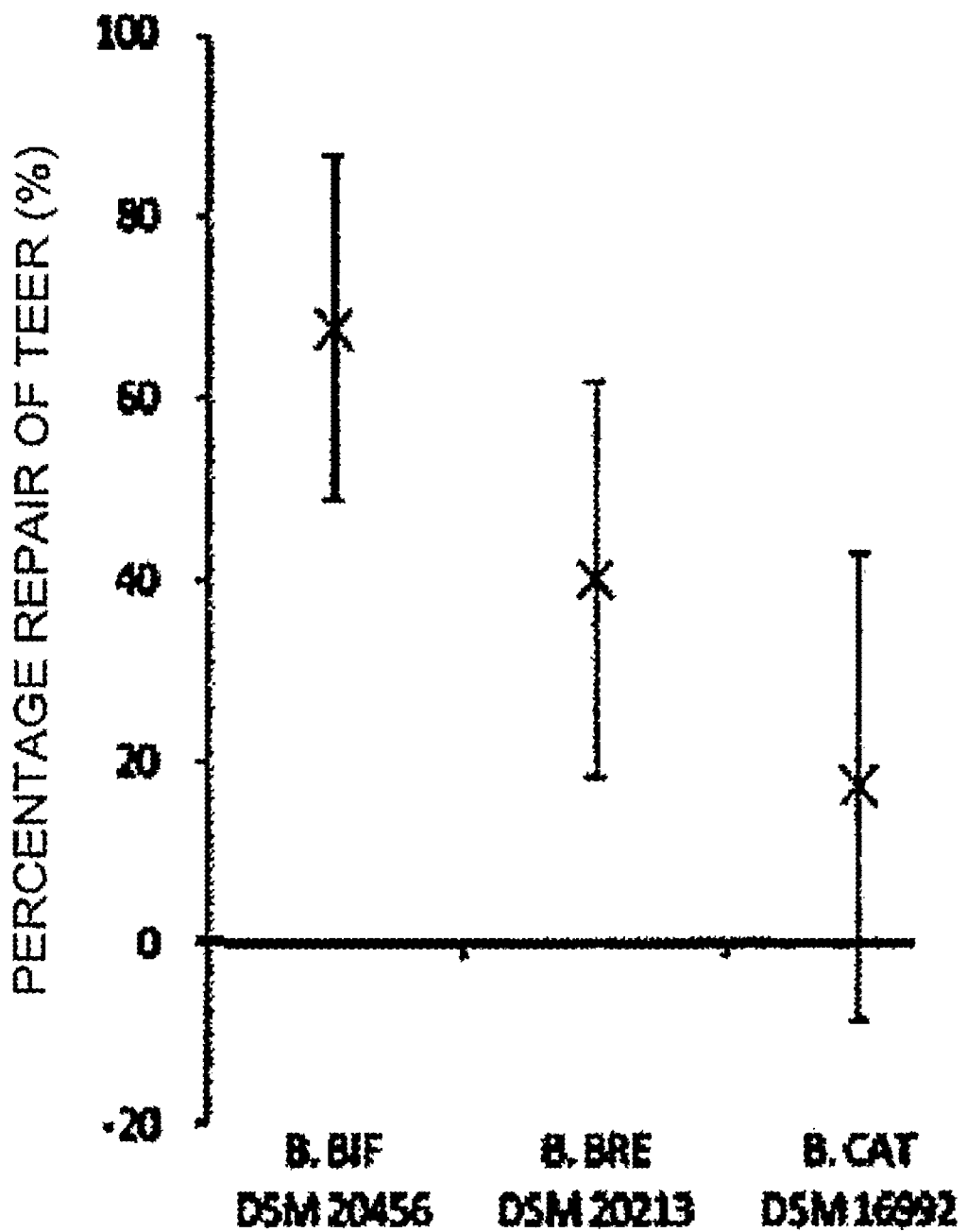
FIG. 7 illustrates the percentage repair of a Caco-2 monolayer by various *Bifidobacterium* bacterial strains (standard strains). The symbol x indicates the average value of three experiments and the error bars show a 95% confidence interval for the average value. The t-test was used for statistical analysis.

Further, the percentage repair of the monolayer by the addition of various standard strains of *Bifidobacterium* spp. was compared (FIG. 7). As a result, *B. bifidum* (DSM20456) and *B. breve* (DSM20213) exhibited significant percentage repair of higher than 40%. Meanwhile, the lower limit of the 95% confidence interval for the average value of the percentage repair by *B. catenulatum* was below 0%, indicating that this bacterial strain did not exhibit a significant repairing effect.

Example 3

A. Materials and Method
(1) Culture of THP-1 Cells

The human monocytic cell line, THP-1 cell, was purchased from DSMZ (Ref. No. ACC 16, Lot No. 19) and cultured in RPMI-1640 MEDIUM (RPMI medium, the product of Sigma-Aldrich Corporation) containing 10% fetal calf serum (FCS, the product of Sigma-Aldrich Corporation).

The THP-1 macrophage monolayer was produced as follows. Into each well of a 96-well MICROTEST™ Tissue Culture Plate (the product of Falcon), 0.1 mL of a $1\times10^6$ cells/mL cell suspension was added (100,000 cells/well). Further, 0.1 mL of PMA (phorbol 12-myristate 13-acetate, the product of Sigma-Aldrich Corporation) adjusted to 20 nM was added, followed by incubation for 48 hours in a $CO_2$ incubator (5% $CO_2$, 95% Air, and 37° C.). The monolayer in which macrophage-like differentiation was induced by PMA was used in the following experiment.

(2) Preparation of Heat-Killed Bacterial Cells

Heat-killed bacterial cells of nine strains of *Bifidobacterium* spp. were used in the experiment (Table 1). The *Bifidobacterium* spp. were cultured at 37° C. for 18 hours in a 1% lactose-added modified GAM medium (the product of Nissui Pharmaceutical Co., Ltd) in an anaerobic glovebox. Upon completion of culture, the bacterial cells were washed by centrifugation with sterile purified water. The washed bacterial cells were suspended in sterile purified water and heated at 100° C. for 30 minutes, and then freeze-dried.

(3) Preparation of Pepsin-Digested Gliadin

Enzymatic digestion of wheat-derived gliadin (the product of Sigma-Aldrich Corporation) was carried out in accordance with the method of Jelinkova, et al. (Jelinkova L, Tuckova L, Cinova J, Flegelova Z, and Tlaskalova-Hogenova H. (2004) Gliadin stimulates human monocytes to production of IL-8 and TNF-α through a mechanism involving NF-κB. FEBS Letters 571: pp. 81 to 85). After suspending 60 mg of gliadin in 100 mL of 0.1 M HCl (pH 1.8), 10 mg of pepsin-agarose (the product of Sigma-Aldrich Corporation) was added, followed by incubation at 37° C. for two hours while shaking. The resulting suspension was centrifuged at 1,500× g for 10 minutes to precipitate pepsin-agarose, and the supernatant was obtained. The supernatant was further centrifuged at 12,000× g for 10 minutes, and the resulting supernatant was obtained. It was freeze-dried and used in the experiment.

(4) Analysis of the Effect of Gliadin and Bacterial Cells on THP-1 Macrophage Cytokines The medium in the upper layer of the THP-1 macrophage monolayer prepared in (1) was discarded by decantation, followed by washing twice with 250 μL of PBS (−) buffer. Further, 0.2 mL of an RPMI medium containing the heat-killed bacterial cells prepared in (2) was added to each well. After incubation for 24 hours in a $CO_2$ incubator, the amount of each cytokine produced was measured. After the measurement, the medium was discarded by decantation, followed by washing twice with 250 μL of PBS (−) buffer, and 0.2 mL of an RPMI medium containing the gliadin prepared in (3) was added to each well. After incubation for 24 hours in a $CO_2$ incubator, the amount of each cytokine (TNF-α and IL-10) produced was measured. For cytokine measurement, the ELISA kit of R&D Systems, Inc. was used. It is to be noted that cells to which only an RPMI medium containing neither gliadin nor bacterial cell was added were used as the negative control and cells to which a medium containing only gliadin was added were used as the positive control.

B. Results

The results of examining the inhibitory effect on the enhanced production of TNF-α by THP-1 macrophages due to gliadin stimulation are shown in Table 1.

As is apparent from Table 1, *B. bifidum* and *B. breve* ($10^{10}$ cells/mL, each) acted to suppress an inflammatory reaction in the lamina propria by inhibiting the enhanced production of TNF-α, which is an inflammatory cytokine. Therefore, it is assumed that these bacteria can be utilized more safely for the prevention or treatment of celiac disease, which is an inflammatory disease.

Meanwhile, *B. adolescentis*, *B. animalis ss. animalis*, *B. animalis ss. lactis*, and *B. catenulatum* ($10^{10}$ cells/mL, each) acted to activate an inflammatory reaction in the lamina propria by aggravating the enhanced production of TNF-α, indicating that they have a risk of exacerbating the inflammatory reaction in celiac disease.

TABLE 1

| Bacterial species | Bacterial strain | Inhibitory effect on enhanced production of TNF-α[1] |
|---|---|---|
| B. adolescentis | YIT 4011$^T$ | − |
| B. animalis ss. animalis | DSM 20104$^T$ | − |
| B. animilis ss. lactis | DSM 10140$^T$ | − |
| B. bifidum | YIT 4007 | + |
|  | YIT 10347 | + |
| B. breve | YIT 4065 | + |
|  | YIT 10001 | + |
|  | YIT 12272 | + |
| B. catenulatum | DSM 16992$^T$ | − |

[1]The inhibitory effect on the enhanced production of TNF-α by THP-1 macrophages due to gliadin stimulation (+: Inhibited, −: Enhanced)

Also, although data are not shown, it was confirmed that *B. breve* YIT10001 increased the amount of IL-10 (anti-inflammatory cytokine) produced by THP-1 macrophages due to gliadin stimulation. Hence, it is considered that the above bacterial strain can be utilized more safely and effectively for the prevention or treatment of celiac disease, which is an inflammatory disease.

The invention claimed is:

1. A method of treating celiac disease comprising administering orally to an individual having the disease a composition comprising lactose and an effective amount of only a single strain of a *Bifidobacterium* or a processed product thereof, wherein the *Bifidobacterium* is selected form the group consisting of *Bifidobacterium breve* and *Bifidobacterium bifidum*, and the processed product is selected from the group consisting of freeze-dried cells of said *Bifidobacterium*, dead bacterial cells of said *Bifidobacterium*, a culture containing the bacterial cells of said *Bifidobacterium* and a combination thereof, wherein the dead bacterial cells are obtained by subjecting live cells of said *Bifidobacterium* to heat treatment or alcohol treatment.

2. The method of claim 1, wherein the *Bifidobacterium* is selected from the group consisting of *Bifidobacterium breve* YIT10001 (FERM BP-8205), *Bifidobacterium breve* YIT4065 (FERM BP-6223), *Bifidobacterium breve* YIT12272 (FERM BP-11320), *Bifidobacterium breve* DSM20213, *Bifidobacterium bifidum* YIT4007 (FERM BP-791), *Bifidobacterium bifidum* YIT10347 (FERM BP-10613), and *Bifidobacterium bifidum* DSM20456.

3. The method of claim 2, wherein the *Bifidobacterium* is *Bifidobacterium breve* YIT10001 (FERM BP-8205).

4. The method of claim 2, wherein the *Bifidobacterium* is contained in a food product.

5. The method of claim 2, wherein the *Bifidobacterium* is contained in a granule, a tablet, or a capsule.

6. The method of claim 2, wherein the *Bifidobacterium* or the processed product is obtained after culturing the *Bifidobacterium* in a growth medium containing milk.

7. The method of claim 2, wherein the effective amount of the live and/or the dead bacterial cells of the *Bifidobacterium* comprises a daily dosage of $10^3$ to $10^{13}$ of the *Bifidobacterium* bacterial cells.

8. A method of treating celiac disease comprising administering orally to an individual having the disease a composition comprising lactose and an effective amount of only a single strain of a *Bifidobacterium* or a processed product thereof, wherein the *Bifidobacterium* is selected form the group consisting of *Bifidobacterium breve* and *Bifidobacterium bifidum*, and the processed product is selected from the group consisting freeze-dried cells of said *Bifidobacterium*, dead bacterial cells of said *Bifidobacterium*, a culture containing the bacterial cells of said *Bifidobacterium* and a combination thereof, wherein the *Bifidobacterium* or the processed product is obtained after culturing the *Bifidobacterium* in a growth medium containing milk and wherein the dead bacterial cells are obtained by subjecting live cells of said *Bifidobacterium* to heat treatment or alcohol treatment.

* * * * *